Sept. 9, 1947. J. W. PEARSON Plant Pat. 760

PEACH TREE

Filed July 1, 1946

WITNESS
Addison J. Avery

INVENTOR
JOHN W. PEARSON
BY Wilfred E. Lawson
ATTY.

Patented Sept. 9, 1947

Plant Pat. 760

UNITED STATES PATENT OFFICE

760

PEACH TREE

John W. Pearson, Lee Pope, Ga.

Application July 1, 1946, Serial No. 680,709

1 Claim. (Cl. 47—62)

The present invention relates to a new and improved variety of peach tree resulting from the mutation of the Early Hiley type peach tree, and having distinct differences from the Early Hiley peach as hereinafter described. The new and distinct variety of peach tree of the Early Hiley type, as herein disclosed, was discovered by me in 1941 in passing through my Early Hiley peach orchard. At that time it was noted that a tree had one limb which bore a different peach from the Early Hiley.

The new and improved variety of the Early Hiley type of peach as observed upon the one limb of the tree matured about ten days earlier than the other fruit upon the other Early Hiley trees in the orchard. This new variety is readily distinguished from the Early Hiley because of its exterior allover intense red color as compared to the pink color of the Early Hiley which is about 25% to 50% pink but is not a bright red like the present new variety.

In the drawing—

Figure 1:
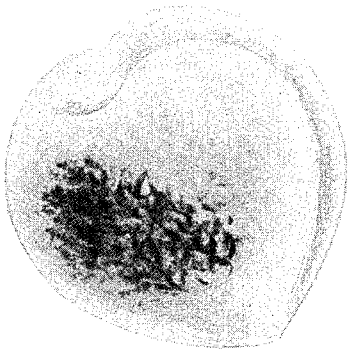
Figure 1 is a view in elevation of the herein described new variety of peach.
Figure 2:
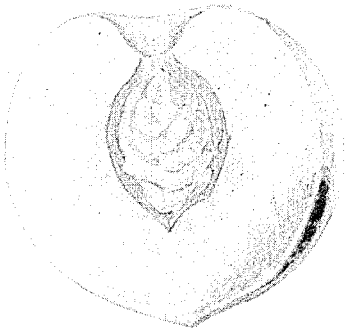
Figure 2 is a view of the inside of one half of the same showing the extent of the coloring of the meat.

The meat of this new variety is also very unusual in the fact that it is freestone and entirely red, such red color extending entirely to the stone. This is very unusual and is the only commercial peach known to the applicant which has red meat. The Early Hiley peach has what is generally called a white meat.

Several thousand trees have been developed asexually from cuttings taken from the one limb upon which the mutations were observed and the trees so propagated have been bearing fruit for the past two years and all of the fruit borne upon the trees propagated from the one limb previously referred to has come true to the sport.

In addition to the previously set forth characteristics of the present new variety, other important features of the present development distinguishing from the Early Hiley are that it is also entirely freestone and that it ripens and is ready for the market as early as ten days before the Early Hiley peach.

Except for the distinctions set forth for the fruit of this new variety, all other identifying characteristics of the tree propagated from the sport limb are the same as the regular Early Hiley tree.

What I claim as new and wish to secure by Letters Patent is:

The new variety of peach tree as herein disclosed characterized by producing fruit similar to the well-known Early Hiley peach except that it is externally of an allover bright red color as compared to the pink color of the Early Hiley fruit; that the meat is entirely red from the skin to the stone; that it is fully ripened and ready for market at least ten days before the Early Hiley peach, and that it is very freestone.

JOHN W. PEARSON.

REFERENCES CITED

The following references are of record in the file of this patent:

UNITED STATES PATENTS

| Number | Name | Date |
|---|---|---|
| Pl. Pt. 161 | Champness | Dec. 17, 1935 |